US012807586B2

(12) United States Patent
Pietraru et al.

(10) Patent No.: US 12,807,586 B2
(45) Date of Patent: Nov. 24, 2026

(54) METHOD FOR PREPARING CYCLIC ANHYDRIDE FROM A LACTONE

(71) Applicants: COMMISSARIAT A L'ENERGIE ATOMIQUE ET AUX ENERGIES ALTERNATIVES, Paris (FR); Centre National de la Recherche Scientifique, Paris (FR)

(72) Inventors: Marie-Hélène Pietraru, Gif-sur-Yvette (FR); Emmanuel Nicolas, Gif-sur-Yvette (FR); Thibault Cantat, Gif-sur-Yvette (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 287 days.

(21) Appl. No.: 18/789,851

(22) Filed: Jul. 31, 2024

(65) Prior Publication Data

US 2025/0042868 A1 Feb. 6, 2025

(30) Foreign Application Priority Data

Aug. 1, 2023 (FR) ...................................... 2308320

(51) Int. Cl.
*C07D 307/60* (2006.01)

(52) U.S. Cl.
CPC .................................. *C07D 307/60* (2013.01)

(58) Field of Classification Search
CPC .................................................... C07D 307/60
See application file for complete search history.

(56) References Cited

FOREIGN PATENT DOCUMENTS

| | | | |
|---|---|---|---|
| EP | 1435354 | A1 | 7/2004 |
| WO | 03/050154 | A2 | 6/2003 |
| WO | 2006/058681 | A2 | 6/2006 |
| WO | 2017/004349 | A2 | 1/2017 |
| WO | 2022/221086 | A1 | 10/2022 |

OTHER PUBLICATIONS

Getzler et al., "Catalytic Cabonylation of beta-Lactones to Succinic Anhydrides," Journal of the American Chemical Society, 126: 6842-6843 (2004).
Mori et al., "Organic Syntheses by Means of Metal Complexes," Bulletin of the Chemical Society of Japan, 42: 777-779 (1969).
Park et al., "Continuous-Flow Production of Succinic Anhydrides via Catalytic beta-Lactone Carbonylation by Co(CO) 4CCr-MIL-101," Journal of the American Chemical Society, 140: 10669-10672 (2018).
Search Report issued in corresponding French Patent Application No. 2308320 dated Jan. 8, 2023.

*Primary Examiner* — Kamal A Saeed
*Assistant Examiner* — Quincy Mckoy
(74) *Attorney, Agent, or Firm* — Morgan, Lewis & Bockius LLP

(57) ABSTRACT

The present invention relates to a method for preparing cyclic anhydride, in particular succinic anhydride and methylsuccinic anhydride from a β-lactone, in particular β-propiolactone and β-butyrolactone, respectively, in the presence of carbon monoxide, catalyzed by dicobalt octacarbonyl [$Co_2(CO)_8$], in an organic solvent.
The invention also relates to the use of this method in the manufacture of food additives, plasticizers, polymers of interest in particular polyesters, polyurethanes and elastanes, resins, coatings, pharmaceutical products.

9 Claims, 1 Drawing Sheet

[Fig. 1]
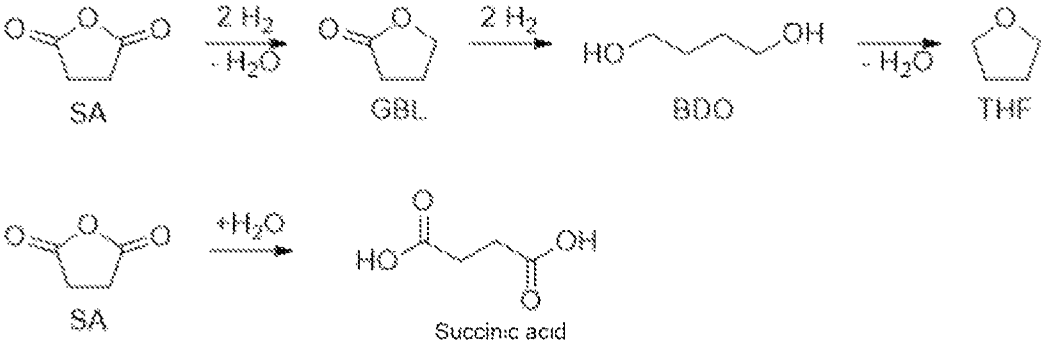
SA GBL BDO THF
SA Succinic acid
[Fig. 2]
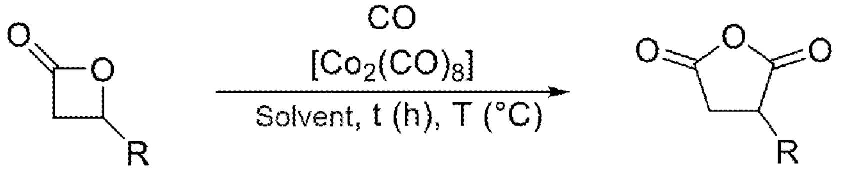
β-lactone
R = H, $CH_3$
Cyclic anhydride
R = H, $CH_3$
(II)
(I)

METHOD FOR PREPARING CYCLIC ANHYDRIDE FROM A LACTONE

TECHNICAL FIELD OF THE INVENTION

The present invention relates to a method for preparing cyclic anhydride, in particular succinic anhydride and methylsuccinic anhydride, from a β-lactone, in particular β-propiolactone and β-butyrolactone, respectively, in the presence of carbon monoxide, catalyzed by dicobalt octacarbonyl [$Co_2(CO)_8$], in an organic solvent.

The invention also relates to the use of this method in the manufacture of food additives, plasticizers, polymers of interest in particular polyesters, polyurethanes and elastanes, resins, coatings, pharmaceutical products.

TECHNICAL BACKGROUND

Succinic anhydride is a molecule of industrial interest. Succinic anhydride is used as a monomer, for example, in the synthesis of aliphatic polyesters via catalytic copolymerization with an epoxide. Succinic anhydride can also be an intermediate in the synthesis of other molecules of interest: its hydration gives the corresponding diacid, succinic acid, and its dehydrogenation gives γ-butyrolactone (GBL) then 1,4-butanediol (BDO), which can in turn be dehydrated into tetrahydrofuran (THF).

These reactions are schematically shown in [FIG. 1].

To the knowledge of the inventors, only two examples describe a method for the synthesis of succinic anhydride by carbonylation of β-propiolactone in the absence of a Lewis acid additive:

- The method described by Tsuji in 1969 (Y. Mori, J. Tsuji, *Bull. Chem. Soc. Jpn.* 1969, 42, 777. doi.org/10.1246/bcsj.42.777). In the presence of [$CO_2$ $(CO)_8$] (2.5 mol %) as a catalyst, under a carbon monoxide pressure of 100 bar, in benzene, β-propiolactone is converted into succinic anhydride with a yield of 29%, after 4 hours at 150° C. Thus, this method gives a modest yield of succinic anhydride, and this under restrictive conditions, in particular in terms of pressure.
- The method described by Novomer (WO2022221086) describing a method for carbonylating an epoxide or a lactone by reacting it with CO in the presence of a catalyst at a temperature higher than 80° C. to form a carbonylation product. Nevertheless, the examples given by the inventors of the present invention show that the catalytic activity is highly dependent on the choice of the combination of some reaction parameters, in particular the pressure and the solvent: in some cases, no catalytic activity is observed; while in others, activity is observed.

Apart from these two examples, the synthesis of succinic anhydride by carbonylation of β-propiolactone has only been described in the literature in the presence of a Lewis acid additive as a co-catalyst.

Any type of Lewis acid has been protected or mentioned in the publications and patent applications filed by the Coates group or the patent applications filed by his company Novomer (Coates G. W. *J. Am. Chem. Soc.* 2004, 126, 6842. doi.org/10.1021/ja048946m; WO 03/050154; US 2007/0213524; WO 2012/158573; WO 2015/138975); This method has been shown to be effective for the carbonylation of lactones into cyclic anhydride. The catalyst and the Lewis acid type additive can be separately introduced, or combined in the form of an ionic salt. The most effective catalysts in terms of activity and/or selectivity generally consist of an anionic metal carbonyl $[Co(CO)_4]^-$ and a cationic Lewis acid of the $[(ligand)M(solvent)_2]^+$ type, with for example, M=Al or Cr;

solvent=THF ligand=salph, oep, tpp (salph: N,N'-bis(3,5-di-tert-butyl-salicylidene)phenyldiamino;

oep: octaethylporphyrin; tpp: tetraphenylporphyrin).

These cationic Lewis acids and corresponding catalysts may require one to several synthesis steps.

This type of Lewis acid associated with the $[Co(CO)_4]^-$ anion was also described in the form of metal-organic frameworks by the Dincă and Román-Leshkov group, and this method was shown to be effective for the carbonylation of lactones into cyclic anhydride (D. P. Hoyoung, M. Dincă, Y. Román-Leshkov, *J. Am. Chem. Soc.* 2018, 140, 10669. doi.org/10.1021/jacs.8b05948).

There is therefore a real need for a method enabling the synthesis of a cyclic anhydride in a sustainable manner from reagents or solvents which can be bio-based and under relatively mild pressure and temperature conditions to reduce the energy consumption necessary for the synthesis of succinic anhydride.

In particular, there is a real need for a method for synthesizing a cyclic anhydride which is easy to implement and industrially interesting.

More particularly, there is a real need for a method for synthesizing a cyclic anhydride which does not require the use of a Lewis acid type additive. All the necessary reagents and solvents should be commercially available, without a prior synthesis step.

SUMMARY OF THE INVENTION

The present invention aims precisely at meeting these needs by providing a method for preparing a cyclic anhydride of formula (I)

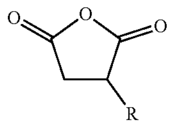

(I)

wherein

R represents a hydrogen atom or a methyl radical, characterized in that a β-lactone of formula (II) is reacted

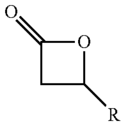

(II)

wherein R represents a hydrogen atom or a methyl radical, with carbon monoxide (CO), in the presence of dicobalt octacarbonyl of formula [$Co_2(CO)_8$] as a catalyst, in one or a mixture of at least two solvent(s) selected from:

- ketones, in particular, acetone, methyl ethyl ketone (MEC), methyl isobutyl ketone (MIBC), cyclohexanone;
- esters, in particular, ethyl acetate, methyl acetate, isopropyl acetate, butyl acetate, isobutyl acetate, isoamyl acetate, glycol diacetate, γ-valerolactone, diethyl succinate;

ethers, in particular, tetrahydrofuran, methyltetrahydrofuran, 1,4-dioxane, anisole, dimethoxyethane, diethyl ether, diisopropyl ether, methyl tert-butyl ether, methyl tert-amyl ether, methyl cyclopentyl ether, ethyl tert-butyl ether;

aromatic hydrocarbons, in particular, toluene, ethylbenzene, m- and p-xylene, mesitylene, styrene;

aprotic polar solvents, in particular, acetonitrile, N,N'-dimethylpropylene urea, dimethyl sulfoxide, sulfolane, nitromethane, dimethyl carbonate, ethylene carbonate, propylene carbonate;

at a temperature lower than or equal to 150° C., and at a total carbon monoxide (CO) pressure lower than or equal to 60 bar.

The conditions under which the method of the invention is implemented are particularly advantageous:

the conditions used are mild, which makes it possible to reduce the energy consumption necessary for the synthesis of the product;

easy separation of cyclic anhydride of formula (I) from the other species of the reaction medium is possible in particular by choosing a solvent in which said cyclic anhydride has a very low solubility.

The appropriate choice of solvent and the application of carbon monoxide pressure are important parameters for implementing the method of the invention.

Furthermore, the method of the invention has the advantage of avoiding the use of a Lewis acid additive.

The invention also relates to the use of this method in the manufacture of food additives, plasticizers, polymers of interest in particular polyesters, polyurethanes and elastanes, resins, coatings, pharmaceutical products.

BRIEF DESCRIPTION OF THE FIGURES

Other features and advantages of the invention will become apparent on reading the following detailed description for the understanding of which reference is made to the appended figures in which:

FIG. 1 represents the use of succinic anhydride (SA) as a starting reagent for the synthesis of other molecules of industrial interest.

FIG. 2 represents the synthesis of a cyclic anhydride of formula (I) from a β-lactone of formula (II), according to the method of the invention.

DETAILED DESCRIPTION OF THE INVENTION

The present invention relates to a method for preparing a cyclic anhydride of formula (I)

(I)

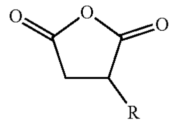

wherein

R represents a hydrogen atom or a methyl radical, characterized in that a β-lactone of formula (II) is reacted (II)

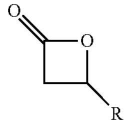

wherein R represents a hydrogen atom or a methyl radical, with carbon monoxide (CO), in the presence of dicobalt octacarbonyl of formula $[Co_2(CO)_8]$ as a catalyst, in one or a mixture of at least two solvent(s) selected from:

ketones, in particular, acetone, methyl ethyl ketone (MEC), methyl isobutyl ketone (MIBC), cyclohexanone;

esters, in particular, ethyl acetate, methyl acetate, isopropyl acetate, butyl acetate, isobutyl acetate, isoamyl acetate, glycol diacetate, γ-valerolactone, diethyl succinate;

ethers, in particular, tetrahydrofuran (THF), methyltetrahydrofuran, 1,4-dioxane, anisole, dimethoxyethane, diethyl ether, diisopropyl ether, methyl tert-butyl ether, methyl tert-amyl ether, methyl cyclopentyl ether, ethyl tert-butyl ether;

aromatic hydrocarbons, in particular, toluene, ethylbenzene, m- and p-xylene, mesitylene, styrene;

aprotic polar solvents, in particular, acetonitrile, N,N'-dimethylpropylene urea, dimethyl sulfoxide, sulfolane, nitromethane, dimethyl carbonate, ethylene carbonate, propylene carbonate;

at a temperature lower than or equal to 150° C., and at a total carbon monoxide (CO) pressure lower than or equal to 60 bar.

Thus, the method of the invention does not require the use of a Lewis acid type additive. All the necessary reagents and solvents are commercially available, without a prior synthesis step.

Other advantages of the method of the invention reside in the mild conditions used to reduce the energy consumption necessary for the synthesis of the product. Furthermore, solvents that are "recommended" in terms of their safety, toxicity, and environmental impact can be used in the method of the invention (Prat, D., Wells, A., Hayler, J., Sneddon, H., McElroy, C. R., Abou-Shehada, S., & Dunn, P. J. *Green Chemistry,* 2016, 18, 288; doi.org/10.1039/C5GC01008J).

The variants of the method of the invention consist of the choice of the solvent, the carbon monoxide pressure, the reaction temperature, the reaction time, the initial lactone concentration and the catalyst loading.

In a preferred embodiment of the invention, the solvent or the mixture of at least two solvent(s) is selected from:

acetone;
ethyl acetate;
1,4-dioxane;
tetrahydrofuran (THF);
anisole;
dimethoxyethane;
acetonitrile;
dimethyl carbonate;
ethylene carbonate;
propylene carbonate; and
toluene.

In another preferred embodiment of the invention, the solvent or the mixture of at least two solvent(s) is selected from:

acetone;
ethyl acetate;
1,4-dioxane;
tetrahydrofuran (THF);
anisole;
dimethoxyethane;
acetonitrile;
dimethyl carbonate; and
toluene.

In another preferred embodiment of the invention, the solvent is acetonitrile.

The total carbon monoxide pressure can vary from 1 bar to 60 bar depending on the solvent, the catalyst loading, the reaction temperature, the lactone concentration, and the desired reaction time.

In one embodiment of the invention, the method of the invention occurs under a total carbon monoxide (CO) pressure of 1 to 60 bar.

In a preferred embodiment of the invention, the method of the invention occurs under a total carbon monoxide (CO) pressure of 5 to 50 bar. In another preferred embodiment of the invention, the total carbon monoxide (CO) pressure is 5 to 20 bar.

The reaction temperature can vary from 30° C. to 150° C. depending on the solvent, the catalyst loading, the lactone concentration and the desired reaction time.

In a preferred embodiment of the invention, the temperature is between 6° and 150° C. In another preferred embodiment of the invention, the temperature is between 6° and 130° C. According to another preferred embodiment of the invention, the temperature is between 9° and 130° C. According to another preferred embodiment of the invention, the temperature is between 9° and 110° C.

In the method of the invention, the quantity of dicobalt octacarbonyl of formula $[Co_2(CO)_8]$, as a catalyst, is from 0.1 to 10 mol %, preferably from 0.5 to 8 mol %, more preferably from 1 to 6 mol %, relative to the quantity of lactone of formula (II). Increasing the quantity of catalyst makes it possible to reduce the reaction time. The concentration of lactone of formula (II) as defined above, can vary from several $mmol \cdot L^{-1}$ to several $mol \cdot L^{-1}$. According to one embodiment of the invention, the concentration of lactone of formula (II) is from 0.01 to 6 M. According to a preferred embodiment of the invention, the concentration of lactone of formula (II) is comprised between 0.1 and 2 M. According to an even more preferred embodiment of the invention, the concentration of lactone of formula (II) is comprised between 0.25 and 1 M.

The reaction time can vary from a few minutes to a few days depending on lactone, the solvent, the catalyst loading, the lactone concentration and the temperature. The duration of the method of the invention is comprised between 30 minutes and 150 hours. Preferably the duration is between 6 and 110 hours.

In one embodiment of the invention, R represents a hydrogen atom.

In another embodiment of the invention, R represents a methyl radical.

When R represents a hydrogen atom, the cyclic anhydride of formula (I) is succinic anhydride and the lactone of formula (II) is β-propiolactone.

When R represents a methyl radical, the cyclic anhydride of formula (I) is methyl succinic anhydride and the lactone of formula (II) is β-butyrolactone.

Furthermore, the method of the invention is intended to be easily applied at the industrial level and to be competitive compared to the methods already implemented on the industrial scale, since it uses dicobalt octacarbonyl $[Co_2(CO)_8]$, already proven in industrial hydroformylation methods, which can be used here under relatively mild pressure and temperature conditions (such as for example, 60 bar or less and 150° C. or less).

Unlike known methods, the method of the invention does not require the addition of an additional additive to improve the performance of the method.

In the context of the invention, "additive" designates a compound which is a Lewis acid, capable of improving the reactivity of the reagents for the transformation of the lactone of formula (II) into cyclic anhydride of formula (I).

Furthermore, another advantage of the method of the invention is the simplicity of its implementation: in addition to the absence of a Lewis acid additive, dicobalt octacarbonyl $[Co_2(CO)_8]$ and the solvent(s) are commercial products and therefore do not require an additional synthesis step. The method is effective at low pressure, in particular, lower than and equal to 60 bar, which is particularly advantageous from an industrial point of view.

The invention also relates to the use of this method in the manufacture of food additives, plasticizers, polymers of interest in particular polyesters, polyurethanes and elastanes, resins, coatings, pharmaceutical products.

EXPERIMENTAL DESCRIPTION OF THE INVENTION

The various reagents, catalysts, additives and solvents directly or indirectly used in the method of the invention in particular, are, in general, commercial compounds/solvents.

Another object of the invention is the use of a method according to the invention, in the manufacture of food additives, plasticizers, polymers of interest in particular polyesters, polyurethanes and elastanes, resins, coatings, pharmaceutical products.

The method for manufacturing food additives, plasticizers, polymers of interest in particular polyesters, polyurethanes and elastanes, resins, coatings, pharmaceutical products, may comprise a step of preparing a cyclic anhydride of formula (I), in particular succinic anhydride, by the method of the invention.

Examples

The various reagents and solvents used in the method of the invention and in the examples are, in general, commercial compounds or can be prepared by any method known to those skilled in the art.

Unless specified, all reactions were carried out under argon, in an anhydrous and inert atmosphere (<5 ppm of $H_2O$ and $O_2$) using conventional schlenk techniques with a vacuum manifold or in a glove box (mBraunLabMaster DP). The glassware was dried for several hours at 120° C. in an oven before use. The reaction solvents were previously dried by usual methods, distilled and stored in an inert atmosphere on a 4 Å molecular sieve. The 4 Å (Aldrich) molecular sieve was previously dried under dynamic vacuum at 250° C. for 48 h before use. All products were purchased from conventional suppliers (Sigma Aldrich, Strem, Alfa-Aesar, Acros, etc.), and previously dried or degassed if necessary. Carbon monoxide comes from Air Products 4.7 purity pressure cylinders.

The synthesized compounds were characterized and quantified by the analysis and mass spectrometry techniques using the instrument Shimadzu GCMS QP2010 Ultra, equipped with a Supelco SLB-ms silica column (30 m×0.25 mm×0.25 μm). The carrier gas is helium (purity 6.0) from Messer. Products were identified by comparison with commercial standards, and calibrated using mesitylene as an internal standard.

Experimental Protocol

1. Under an inert atmosphere, dicobalt octacarbonyl [$Co_2(CO)_8$] is dissolved in the solvent. Depending on the solvent used, a gas evolution may be observed. The lactone is then added. In order to monitor the yield of cyclic anhydride and the lactone conversion, an internal standard such as mesitylene can be added.
2. The reaction mixture is introduced into an autoclave previously purged three times with a carbon monoxide flow. The autoclave contains a glass tube to collect the reaction mixture and is provided with a magnetic stirrer.
3. The autoclave is then sealed, and carbon monoxide is injected into the autoclave up to the desired total pressure.
4. The autoclave is placed in a heating block under magnetic stirring.
5. The reaction is stopped by dipping the autoclave in an ice bath.
6. Once the autoclave is at room temperature (20±5° C.), it can be opened, and the reaction mixture can be analyzed.

The described conversions and yields are measured in GC-MS (Gas Chromatography—Mass Spectrum) using an internal standard added at the start of the reaction, mesitylene, for which a calibration curve was previously carried out.

Example 1

Dicobalt octacarbonyl (17.1 mg; 0.05 mmol; 0.05 eq) is dissolved in acetonitrile (2 mL). A gas evolution is observed and lasts approximately 20 min. Mesitylene (14 μL; 0.1 mmol; 0.1 eq) and β-propiolactone (63 μL; 1 mmol; 1 eq) are then added to the reaction mixture. The reaction mixture is introduced into the autoclave which is purged three times by a carbon monoxide flow. The autoclave is sealed and subjected to a carbon monoxide pressure of 15 bar, then placed under magnetic stirring for 6 h in a heating block at 90° C. After analysis of a reaction crude sample by GC-MS, 100% of β-propiolactone was converted, for a yield of succinic anhydride of 99%.

Example 2

Dicobalt octacarbonyl (17.1 mg; 0.05 mmol; 0.05 eq) is dissolved in acetonitrile (2 mL). A gas evolution is observed and lasts approximately 20 min. Mesitylene (14 μL; 0.1 mmol; 0.1 eq) and β-butyrolactone (86.1 mg; 1 mmol; 1 eq) are then added to the reaction mixture. The reaction mixture is introduced into the autoclave which is purged three times by a carbon monoxide flow. The autoclave is sealed and subjected to a carbon monoxide pressure of 15 bar, then placed under magnetic stirring for 39 h in a heating block at 110° C. After analysis of a reaction crude sample by GC-MS, 87% of β-butyrolactone was converted, for a yield of methylsuccinic anhydride of 67%.

Tests Carried Out:

The yield of cyclic anhydride and the conversion of lactone were obtained by GC-MS, following a calibration carried out with commercial samples of cyclic anhydride and lactone. Percentage values are given with an uncertainty of +/−5 percentage points.

For the carbonylation of β-propiolactone into succinic anhydride (Table 1), the following can be noted:

- In acetone, 1,4-dioxane, toluene, anisole, dimethyl carbonate, and ethyl acetate, decreasing the pressure induces an increase in yield (Table 1, entries 1-7 and 24-35). In particular, increasing the pressure to 50 bar induces a loss of activity in 1,4-dioxane, anisole and dimethyl carbonate (Table 1, entries 7, 29 and 32), and this loss of activity is observed from 15 bar in toluene (Table 1, entries 25 and 26).
- In dimethoxyethane, the pressure has no influence on the yield (Table 1, entries 8-10).
- DMF is an unsuitable solvent for the method, regardless of the pressure tested (Table 1, entries 11-13).
- In acetonitrile and THF, increasing the pressure from 5 to 15 bar induces the increase in yield, but the increase from 15 to 50 bar induces a decrease in yield (Table 1, entries 14-17 and 21-23). For these two solvents, a moderate pressure is therefore preferable.
- The optimal conditions for the method consist of the use of acetonitrile as a solvent, at a pressure of 15 bar, where a quantitative yield of anhydride is observed after 6 h (Table 1, entry 16).

The results of the different experiments have been presented in the following tables.

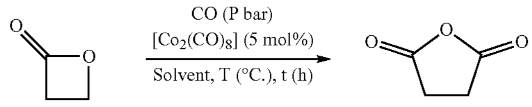

β-propiolactone
0.5 mol.L$^{-1}$

Succinic anhydride

TABLE 1

| Entry | Solvent | T (° C.) | P (bar) | t (h) | Yield of succinic anhydride (%) |
|---|---|---|---|---|---|
| 1 | Acetone | 90 | 5 | 6 | 77 |
| 2 | Acetone | 90 | 15 | 6 | 57 |
| 3 | Acetone | 90 | 15 | 15 | 79 |
| 4 | Acetone | 90 | 50 | 6 | 29 |
| 5 | 1,4-dioxane | 90 | 5 | 6 | 76 |
| 6 | 1,4-dioxane | 90 | 15 | 6 | 38 |
| 7 | 1,4-dioxane | 30 | 50 | 6 | <5 |
| 8 | Dimethoxyethane | 90 | 5 | 6 | 74 |
| 9 | Dimethoxyethane | 90 | 15 | 6 | 76 |
| 10 | Dimethoxyethane | 90 | 50 | 6 | 71 |
| 11 | N,N-dimethylformamide | 90 | 5 | 6 | <5 |
| 12 | N,N-dimethylformamide | 90 | 15 | 6 | <5 |
| 13 | N,N-dimethylformamide | 90 | 50 | 6 | <5 |
| 14 | Acetonitrile | 90 | 5 | 6 | 73 |
| 15 | Acetonitrile | 90 | 15 | 3 | 92 |
| 16 | Acetonitrile | 90 | 15 | 6 | 99 |
| 17 | Acetonitrile | 90 | 50 | 6 | 38 |
| 18 | Acetonitrile | 110 | 15 | 1 | 83 |
| 19 | Acetonitrile | 110 | 15 | 3 | 87 |
| 20 | Acetonitrile | 130 | 15 | 1 | 65 |
| 21 | Tetrahydrofuran | 80 | 5 | 6 | 69 |
| 22 | Tetrahydrofuran | 90 | 15 | 6 | 83 |
| 23 | Tetrahydrofuran | 90 | 50 | 6 | 58 |
| 24 | Toluene | 90 | 5 | 6 | 44 |
| 25 | Toluene | 90 | 15 | 6 | <5 |
| 26 | Toluene | 98 | 50 | 6 | <5 |
| 27 | Anisole | 90 | 5 | 6 | 38 |

TABLE 1-continued

| Entry | Solvent | T (° C.) | P (bar) | t (h) | Yield of succinic anhydride (%) |
|---|---|---|---|---|---|
| 28 | Anisole | 90 | 15 | 6 | 13 |
| 29 | Anisole | 90 | 50 | 6 | <5 |
| 30 | Dimethyl Carbonate | 90 | 5 | 6 | 51 |
| 31 | Dimethyl Carbonate | 90 | 15 | 6 | 13 |
| 32 | Dimethyl Carbonate | 90 | 50 | 6 | <5 |
| 33 | Ethyl acetate | 90 | 5 | 6 | 76 |
| 34 | Ethyl acetate | 90 | 15 | 6 | 37 |
| 35 | Ethyl acetate | 90 | 50 | 6 | 16 |
| 36[a] | Acetonitrile | 90 | 15 | 18 | 92 |
| 37[b] | Acetonitrile | 90 | 15 | 72 | 60 |

[a]2.5 mol % of [$Co_2(CO_8)$] are used.
[b]1 mol % of [$Co_2(CO_8)$] is used.

Table 1—Carbonylation of β-Propiolactone into Succinic Anhydride

For the carbonylation of β-butyrolactone into methylsuccinic anhydride (Table 2), the following can be noted:

at 90° C., little activity is observed (Table 2, entry 1).

increasing the temperature to 110 or 130° C. makes it possible to observe the formation of the anhydride, but a temperature of 110° C. is preferable for better yield (Table 2, entries 2-4).

increasing the pressure to 50 bar causes a decrease in yield (Table 2, entries 5 and 6).

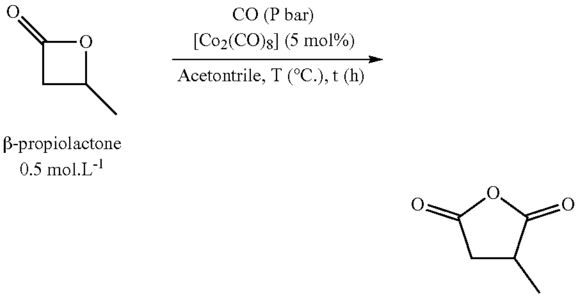

β-propiolactone
0.5 mol.L[-1]

Methylsuccinic anhydride

TABLE 2

| Entry | P (bar) | T (° C.) | t (h) | Yield of methylsuccinic anhydride (%) |
|---|---|---|---|---|
| 1 | 15 | 90 | 6 | <5 |
| 2 | 15 | 110 | 16 | 48 |
| 3 | 15 | 110 | 39 | 67 |
| 4 | 15 | 130 | 39 | 38 |
| 5 | 50 | 110 | 16 | 31 |
| 6 | 50 | 110 | 72 | 34 |

Table 2—Carbonylation of β-Butyrolactone into Methylsuccinic Anhydride

The tests that the inventors carried out in the laboratory show that the combination of some parameters does not make it possible to obtain more than 5% yield of succinic anhydride or methylsuccinic anhydride. In other words, the combination of some parameters only allows very low or zero catalytic activity to be observed (Table 1, Table 2). More precisely, the inventors noted a very low catalytic activity in the following cases, using [$Co_2(CO)_8$] as a catalyst for the carbonylation of β-propiolactone, after heating at 90° C. for 6 h (Table 1):

in 1,4-dioxane, at 50 bar (Table 1, entry 7);

in dimethyl carbonate, at 50 bar (Table 1, entry 32);

in N,N-dimethylformamide, at 5, 15 and 50 bar (Table 1, entries 11 to 13);

in toluene, at 15 and 50 bar (Table 1, entries 24 and 25).

Similarly, for the carbonylation of β-butyrolactone, catalyzed by [$Co_2(CO)_8$] in acetonitrile at 15 bar, a very low activity was observed after 6 h at 90° C. (Table 2, entry 1).

Conversely, the inventors have shown that a judicious combination of parameters makes it possible to observe a high catalytic activity. This is illustrated by the other catalytic tests described for the carbonylation of β-propiolactone in Table 1:

acetone and ethyl acetate make it possible to obtain good yields of succinic anhydride at any pressure, but in particular at low pressure (77% and 76% at 5 bar, Table 1, entries 1 and 33);

1,4-dioxane, anisole and dimethyl carbonate make it possible to obtain a moderate or good yield, at low or moderate pressure (13 to 76%, Table 1, entries 5, 6, 27, 28, 30 and 31);

dimethoxyethane makes it possible to obtain a good yield at any pressure (71 to 76%, Table 1, entries 8 to 10);

acetonitrile makes it possible to obtain a moderate to very good yield at any pressure (38 to 99%, Table 1, entries 14 to 20); in particular, a quantitative yield of succinic anhydride is observed under 15 bar of carbon monoxide, after 6 h of reaction at 90° C. (Table 1, entry 16);

tetrahydrofuran makes it possible to obtain a moderate to very good yield at any pressure (58 to 83%, Table 1, entries 21 to 23); the highest yield is observed at 15 bar (83%, Table 1, entry 22);

toluene makes it possible to obtain a moderate yield at low pressure (44%, Table 1, entry 24).

These catalytic results illustrate that the combinations of the two parameters "solvent" and "pressure" are not obvious, since no clear and systematic trend emerges. Some solvents are not effective at any pressure (N,N-dimethylformamide), others are effective at any pressure (dimethoxyethane), others are all the more effective as the pressure is low (acetone, 1,4-dioxane), toluene, anisole, dimethyl carbonate, ethyl acetate), and others are more effective at moderate pressure (acetonitrile, tetrahydrofuran).

The invention claimed is:

1. A method for preparing a cyclic anhydride of formula (I)

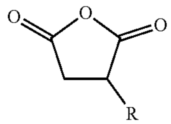

(I)

wherein

R represents a hydrogen atom or a methyl radical, characterized in that a -lactone of formula (II) is reacted

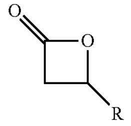

(II)

wherein R represents a hydrogen atom or a methyl radical, with carbon monoxide (CO), in the presence of dicobalt octacarbonyl of formula $[Co_2(CO)_8]$ as a catalyst, in one or a mixture of at least two solvent(s) selected from:

acetone;
ethyl acetate;
1,4-dioxane;
tetrahydrofuran (THF);
anisole;
dimethoxyethane;
acetonitrile;
dimethyl carbonate; and
toluene at a temperature of 30 to 150° C., and at a total carbon monoxide (CO) pressure of 1 to 60 bar.

2. The method according to claim 1, wherein the solvent is acetonitrile.

3. The method according to claim 1, wherein it occurs under a total carbon monoxide (CO) pressure of 3 to 50 bar.

4. The method according to claim 1, wherein it occurs at a temperature comprised between 6° and 150° C.

5. The method according to claim 1, wherein the quantity of dicobalt octacarbonyl of formula $[Co_2(CO)_8]$, is from 0.1 to 10 mol %, relative to the quantity of lactone of formula (II).

6. The method according to claim 1, wherein the concentration of lactone of formula (II) is from 0.01 to 6 M.

7. The method according to claim 1, wherein the duration of the method is comprised between 30 minutes and 150 hours.

8. The method according to claim 1, wherein R represent a hydrogen atom.

9. The method according to claim 1, wherein R represent a methyl radical.

* * * * *